United States Patent

Takaki et al.

[11] Patent Number: 5,859,033
[45] Date of Patent: *Jan. 12, 1999

[54] ANTICONVULSANT PYRIDINYL BENZAMIDE DERIVATIVES

[75] Inventors: Katherine S. Takaki, Middletown; Astrid Ortiz, Fairfield, both of Conn.; Brett T. Watson, Vaerloese, Denmark

[73] Assignee: Bristol-Myers Squibb Company, Princeton, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 838,764

[22] Filed: Apr. 10, 1997

Related U.S. Application Data

[60] Provisional application No. 60/017,565 May 14, 1996.
[51] Int. Cl.$^6$ .................. A61K 31/44; C07D 211/72; C07D 211/84; C07D 211/70
[52] U.S. Cl. ................. 514/357; 514/352; 546/309; 546/337
[58] Field of Search .................... 514/352, 357; 546/309, 337

[56] References Cited

U.S. PATENT DOCUMENTS

| | | |
|---|---|---|
| 3,252,986 | 5/1966 | Gadekar . |
| 4,093,734 | 6/1978 | Kruger et al. . |
| 4,684,748 | 8/1987 | Robertson . |
| 4,981,866 | 1/1991 | Beedle et al. . |

OTHER PUBLICATIONS

Metz, et al., "Cloxacepride and Related Compounds: A New Series of Orally Active Antiallergic Compounds," *J. Med. Chem.*, 1983, 26/Jul., pp. 1065–1070.

*Primary Examiner*—William R. A. Jarvis
*Attorney, Agent, or Firm*—Richard P. Ryan

[57] ABSTRACT

A series of pyridinyl tri-substituted benzamide derivatives of general structure

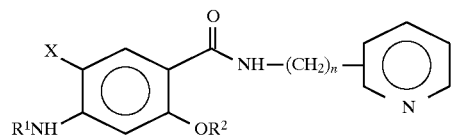

wherein the symbols $R^1$, $R^2$, X and n are described in detail in the specification, are useful as anticonvulsants agents.

10 Claims, No Drawings

ANTICONVULSANT PYRIDINYL BENZAMIDE DERIVATIVES

BACKGROUND OF THE INVENTION

This application claims the benefit of U.S. provisional application 60/017,565, filed May 14, 1996.

The invention pertains to novel pyridinyl benzamide derivatives having drug and bio-affecting properties and to their preparation, pharmaceutical formulations and use. In particular, the invention concerns tri-substituted benzamides having a pyridine ring, with and without an alkyl linker, attached to the amide nitrogen. These compounds possess potent anticonvulsant properties that should make them useful in treating certain medical disorders.

The anticonvulsant drugs currently available in the United States have several shortcomings as therapeutic agents. About one of every three patients does not obtain significant relief from seizures and a number of side-effects accompany the therapeutic effects obtained. An underlying reason for the high incidence of side-effects is that most current anticonvulsant agents possess low therapeutic ratios. For this reason, new anticonvulsants, which may possess greater selectivity and less toxicity in a clinical population, are needed.

A large number of various benzamide derivatives are known and the use of many of them as medicinals has been disclosed.

A number of amino-substituted benzamides have been disclosed as anticonvulsant agents. In general, these disclosed compounds have structural formula 1, wherein Z is a substituted phenyl or phenylalkyl moiety.

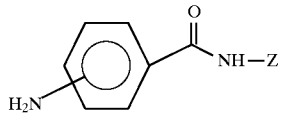

For example, Robertson claims anticonvulsants, 2, in U.S. Pat. No. 4,684,748;

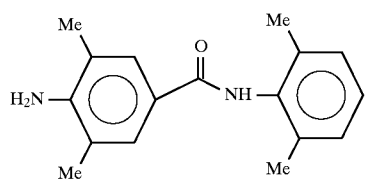

and in U.S. Pat. No. 4,981,866, Beedle and Robertson claim the use of various mono-substituted benzamide derivatives, 3, as anticonvulsants.

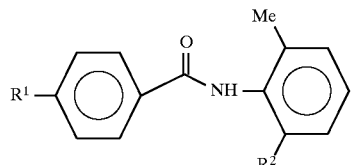

In formula 3, $R^1$ can also be hydroxy, alkoxy and alkyl in addition to being substituted amino.

While a number of pyridinyl benzamide derivatives are known, they are not tri-substituted benzamides and have not been particularly disclosed for use as anticonvulsant agents. These known pyridinyl benzamide compounds conform to the general structural formula 4. In 4, $R^1$ can be hydrogen, halogen, alkyl, alkoxy, amino and nitro; $R^2$ is generally amino;

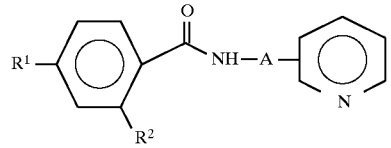

and A is a chemical bond or an alkyl linking group.

As an example, Gadekar in U.S. Pat. No. 3,252,986 discloses a series of tranquilizers-muscle relaxants including compounds of formula 5.

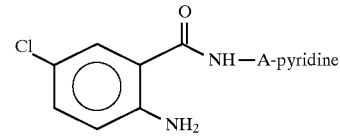

Similarly, Wright and Tomcufcik describe a series of pyridinyl benzamides of formula 6 disclosed as cardioprotective agents and inhibitors of thromboxane synthetase. In 6, R is hydrogen, alkyl,

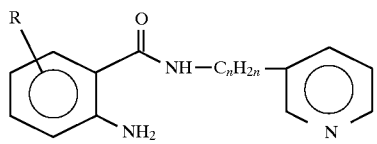

alkoxy, or nitro; and n is 2 to 5.

Kruger, et al. in U.S. Pat. No. 4,093,734 disclose a subset of pyridinyl benzamides of formula 7 described as being useful anxiolytics, anticonvulsants, antiemetics, and antiulceragenics.

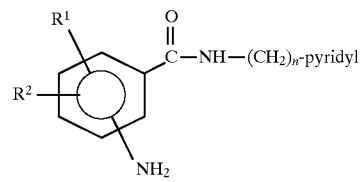

In 7, $R^1$ is hydrogen or halogen and $R^2$ is methyl, halogen or nitro.

Of less significance are disclosures of metaclopramide-type benzamide derivatives having antiemetic and gastroprokinetic properties. Monkovic, et al., are typical in disclosing a series of antiemetic tri-substituted benzamides, 8, in which

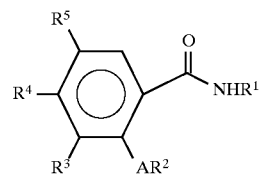

$R^1$ is a basic moiety such as $-CH_2)_n-NR^7R^8$ or

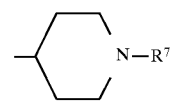

These foregoing references do not teach or suggest the specific novel pyridinyl tri-substituted benzamide derivatives of the present invention nor the anticonvulsant use of these compounds.

SUMMARY AND DETAILED DESCRIPTION OF THE INVENTION

In its broadest aspect, the present invention is concerned with specific tri-substituted pyridinylbenzamide derivatives having useful anticonvulsant properties. In this regard, the invention encompasses novel compounds of Formula I, their pharmaceutical formulations and their use as anticonvulsant agents.

In Formula I,

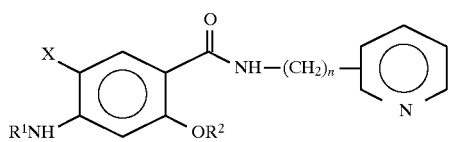

$R^1$ is selected from hydrogen, lower acyl and lower alkyl; $R^2$ lower alkyl;
X is halogen; and
n is zero or an integer from 1 to 4.

The term "lower" as used for lower acyl and lower alkyl refers to the number of carbon atoms contained in the functional group and should be understood to comprise from one to four carbon atoms; e.g., formyl to butanoyl and methyl to butyl. "Halogen" refers to fluorine, chlorine, bromine and iodine. As can be seen from the definition of n, the pyridine moiety can be directly bonded to the amide nitrogen or can be linked by an alkanediyl group of from one to four methylene units.

Preferred classes of compounds of Formula I are those wherein $R^1$ is hydrogen, $R^2$ is methyl, X is chloro and n is 1.

Additionally, compounds of Formula I also encompass all pharmaceutically acceptable acid addition salts and/or solvates, particularly hydrates, thereof. The present invention also encompasses any and all isomers of compounds of Formula I.

The pharmaceutically acceptable acid addition salts of the invention are those in which the counter-ion does not contribute significantly to the toxicity or pharmacological activity of the salt and, as such, they are the pharmacological equivalents of the bases of Formula I. They are generally preferred for medical usage. In some instances, they have physical properties which make them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid preferably by contact in solution employing an excess of commonly used inert solvents such as water, ether, benzene, methanol, ethanol, ethyl acetate and acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, mandelic, phosphoric, nitric, mucic, isethionic, palmitic, heptanoic and others.

The compounds of Formula I can be prepared by means of the process shown in Scheme 1. $R^1$, $R^2$, X and n are as previously described.

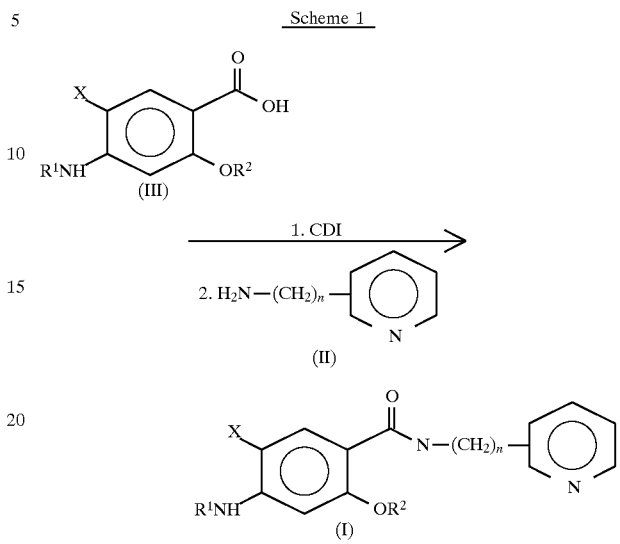

In a straightforward manner, a starting tri-substituted benzoic acid (III) is coupled with an appropriate starting pyridinyl amine (II) by using 1,1-carbonyldiimidazole (CDI) or another peptide coupling agent (e.g. 1,3-dicyclohexylcarbodiimide, or the like) in a suitable reaction solvent with heating. In practice, the use of CDI in refluxing tetrahydrofuran (THF) is preferred for production of products (I). It would be understood that certain variations in the process could be made affording similar Formula I compounds. Similarly, other variations in reagents, solvents, and reaction conditions for the Scheme I process would be known to one skilled in the art. The various starting materials of Formulas II and III are, in general, commercially available. They may also be synthesized using procedures readily available in the chemical literature.

The above processes may be adapted to variation in order to produce other compounds embraced by this invention but not specifically disclosed. Variations of the methods to produce the same compounds in somewhat different fashion will also be evident to one skilled in the art. To provide greater descriptive detail, representative synthetic examples are set out in the "Description of Specific Embodiments" section hereinbelow.

The compounds of Formula I are anticonvulsant agents. Their anticonvulsant properties were determined by pharmacologic testing, utilizing two standard animal models of epilepsy: the pentylenetetrazole (PTZ)-induced seizure procedure and the maximal electroshock test (MES). General descriptions of such testing can be found in J. F. Reinhard and J. F. Reinhard, Jr., "Experimental Evaluation of Anticonvulsants," in *Anticonvulsants*, J. A. Vida, Ed., Academic Press, New York, N.Y., 1977.

The anticonvulsant tri-substituted benzamide pyridine derivatives of Formula I may be administered by various routes including the oral, rectal, transdermal, subcutaneous, intravenous, intramuscular, or intranasal routes, being usually employed in the form of a pharmaceutical composition. The invention includes a pharmaceutical composition comprising from about 1% to about 95% by weight of a compound of Formula I, or a pharmaceutically acceptable acid addition salt thereof, associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 2.5 to 500 mg, more usually 25 to 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg/kg of body weight. In the treatment of adult humans, the range of about 1 to 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

For treating epilepsy, a compound of Formula I may be employed as a daily dosage in the range of about 50 mg to about 2000 mg, usually in 1 to 4 divided dosages, for an average adult human. A unit dosage would contain about 2.5 mg to about 500 mg of the active ingredient.

In general, compounds of Formula I may be used in treating epilepsy in mammals including humans in a manner similar to that used for phenytoin. Medical aspects of the treating of epilepsy are described in greater detail by Rail and Schleifer in *Goodman and Gilman's The Pharmacological Basis of Therapeutics*, 8th ed.; Goodman Gilman, A.; Rail, T. W.; Nies, A. S.; Taylor, P., Eds.; Pergamon Press: New York, 1990; pp. 436–462.

DESCRIPTION OF SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonances (NMR) are spectral characteristics refer to Chemical shifts ($\delta$) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as a broad singlet (bs), singlet (s), multiplet (m) or doublet (d). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

The following examples describe in detail the preparation of compounds of Formula I. It will be apparent to those skilled in the art that modifications, both of materials and methods, will allow preparation of other compounds disclosed herein. From the foregoing description and the following examples it is believed that one skilled in the art is able to use the invention to the fullest extent.

COMPOUNDS OF FORMULA I

EXAMPLE 1

General Method: 4-Amino-5-chloro-2-methoxy-N-(3-pyridinylmethyl)benzamide

To a solution of 4-amino-5-chloro-2-methoxybenzoic acid (1.0 eq) in THF was added CDI (1.0 eq) and this was heated to reflux under nitrogen for 20 min. To this was added the 3-pyridinylmethylamine (1.0 eq) in THF (10 ml) and the reaction was heated to reflux overnight. The solvent was removed in vacuo and the resultant solid was purified by recrystallization from acetonitrile. The free base was characterized as follows: m.p. 158°–161° C.; 1H NMR (300 MHz, CDCl$_3$) $\delta$ 8.56 (s,1H), 8.48 (d, J=3 Hz, 1H), 8.10 (s, 1H), 8.02 (bd, J=6 Hz, 1H), 7.66 (m, 1H), 7.23 (m,1H), 6.26 (s,1H), 4.62 (d, J=6 Hz, 2H), 4.43 (bs, 2H), 3.83 (s, 3H); $^{13}$C NMR (75 MHz, CDCl$_3$) $\delta$ 164.7,157.5,148.9, 148.6, 146.9, 135.5, 134.7, 133.3, 123.5, 111.9, 111.7, 97.7, 56.1, 41.1; IR (KBr) 3400, 1650, 1545, 1270, 750 cm$^{-1}$; MS (DCI) m/e 583 (MH+M), 292 (MH); Analysis calc'd for $C_{14}H_{14}N_3O_2Cl_1$: C, 57.64; H, 4.84; N, 14.40; found: C, 57.39; H, 4.77; N, 14.31.

The hydrochloride salt was prepared by adding ethanolic HCl to an acetonitrile solution of the free base. Characterization of the HCl salt: m.p.>220° C.; $^1$H NMR (300 MHz, DMSO-$d_6$) $\delta$ 8.82 (s, 2H), 8.80 (s, 1H), 8.73 (t, J=6 Hz, 1H), 8.02 (dd, J=6, 9Hz, 1H), 7.65 (s, 1H), 6.51 (s, 1H), 4.63 (d, J=6 Hz, 2H), 3.84 (s, 3H); $^{13}$C NMR (75 MHz, DMSO-$d_6$) $\delta$ 164.311, 157.69, 148.91, 144.66, 140.31, 139.94, 131.65, 126.88, 109.52, 108.85, 97.33, 55.86; IR (KBr) 3200, 2500, 1640, 1555, 1255, 775 cm$^{-1}$; MS (DCI) m/e 292 (MH); Analysis calc'd for $C_{14}H_{15}N_3O_2Cl_2$: C, 51.24; H, 4.61; N, 12.80; found: C, 51.30; H, 4.59; N, 12.89.

EXAMPLE 2

4-Amino-5-chloro-2-methoxy-N-(2-pyridinylmethyl)benzamide

Prepared analogously to the general procedure using 2-aminomethylpyridine. m.p. 161°–1630° C.; $^1$H NMR (300

MHz, CDCl$_3$) δ 8.68 (bs, 1H), 8.51 (m, 1H), 8.08 (s, 1H), 7.60 (m, 1H), 7.29 (d, J=6 Hz, 1H), 7.14 (m, 1H), 6.26 (s, 1H), 4.72 (d, J=3 Hz, 2H), 4.83 (bs, 2H), 3.84 (s, 3H); $^{13}$C NMR (75 MHz, CDCl$_3$) δ 164.6, 157.7, 157.6, 149.0, 146.9, 136.7, 133.0, 122.1, 122.0, 112.2, 111.4, 97.8, 56.1, 45.2; IR (KBr) 3500, 1650, 1540, 1250, 765 cm$^{-1}$; MS (DCI) m/e292 (MH); Analysis calc'd for $C_{14}H_{14}N_3O_2Cl_1$: C, 57.64; H, 4.84; N, 14.40; found: C, 57.75; H, 4.84; N, 14.40.

EXAMPLE 3

4-Amino-5-chloro-2-methoxy-N-(4-pyridinylmethyl) benzamide

Free base prepared analogously to the general procedure using 4-aminomethylpyridine. m.p. 160°–1620° C.; $^1$H NMR (300 MHz, CDCl$_3$) δ 8.50 (bs, 2H), 8.08 (s, 2H), 7.20 (d, J=6 Hz, 2H), 6.28 (s,1H), 4.61 (d, J=6 Hz, 2H), 4.45 (bs, 2H), 3.84 (s, 3H); $^{13}$C NMR (75 MHz, CDCl$_3$) δ 164.9, 157.6, 149.8, 148.3, 147.2, 133.3, 122.1, 111.6, 97.7, 56.2, 42.5; IR (KBr) 3450, 1640, 1540, 1250, 830 cm$^{-1}$; MS (DCI) m/e 583 (MH+M), 292 (MH); Analysis calc'd for $C_{14}H_{14}N_3O_2Cl_1$: C, 57.64; H, 4.84; N, 14.40; found: C, 57.66; H, 4.75; N, 14.51.

MEASUREMENT OF ANTICONVULSANT PROPERTIES

EXAMPLE 4

The Maximum Electroshock (MES) Procedure

In the MES procedure a tonic seizure was produced in female C57Bl/6 mice (17–26 g) by the delivery of a 50 milliamps current through corneal electrodes for 0.2 sec. Before testing, animals were allowed food and water ad libitum. Compounds were injected i.p. (vol=0.1 mL/20 g) 30 min. before the MES. Reference compounds (phenytoin, carbamazepine, phenobarbital, and valproic acid) were tested at the time of peak activity and at the dose range reported in the literature. Seven mice were used per group. In this test anticonvulsive activity was indicated by the abolition of the hindlimb tonic extension. The median effective dose (ED$_{50}$) was obtained for each compound.

EXAMPLE 5

The Pentylenetetrazole (PZT)-Induced Seizure Procedure

In the PTZ procedure female C57Bl/6 mice (17–26 g) were injected i.p. (vol=0.1 mL/20 g) with test compound or vehicle 30 min. before i.p. administration of 75 mg/kg pentylenetetrazol. Multiple doses of reference compounds (ethosuximide, trimethadione, and pentobarbital) were tested at the time of peak activity and at the dose range reported in the literature. Ten mice were used per group. After injection, mice were placed in individual observation cages and monitored for one hour. During the first 30 minutes following PTZ injection, seizure activity was recorded by measuring: the latency to the onset of pre-convulsive activity, the latency to the onset of the first clonic seizure longer than five seconds, the latency to the onset of the first intense-generalized clonic/tonic seizure, and the length of survival. During the second 30 min. period, only time of death was recorded. Those compounds that produced a significant delay in the onset of seizure activity or delayed (or abolished) mortality when compared to that produced by vehicle were classified as anticonvulsants. Significant difference between animals treated with vehicle or test compound were determined using the Student's t-test.

The anticonvulsant activity of some selected compounds of Formula I is displayed in Table 2.

TABLE 2

Summary of Anticonvulsive Activity of Some Selected Formula I Benzamides

| | | PTZ Anticonvulsive Results* | | | | |
|---|---|---|---|---|---|---|
| Ex. # | MES** Results | Pre | First | Surv Time | IGS | Surv |
| 1 | + | ++ | ++++ | ++++ | +++ | ++++ |
| 2 | NT | ++ | ++++ | +++ | NT | ++++ |
| 3 | +++ | ++ | ++++ | ++++ | +++ | ++++ |

*50 mg/kg i.p. For PTZ results: + = > 100% of controls;
++ = > 200% of controls; +++ = > 300% of controls;
++++ = > 400% of controls
**For MES results: median effective dose (ED$_{50}$): + = < 75 mg/kg;
++ = < 25 mg/kg; +++ = < 10 mg/kg
Pre: latency to first twitch
First: latency to first seizure
Surv Time: duration of survival
IGS: onset of intense, generalized seizures
Surv: survival at one hour post-PTZ
MES: maximum electroshock
NT: not tested

We claim:

1. The compound of Formula I and its pharmaceutically

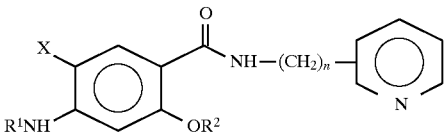

acceptable salts and hydrates thereof,
wherein
R$^1$ is selected from hydrogen, lower acyl, and lower alkyl;
R$^2$ is lower alkyl;
X is halogen; and
n is zero or an integer selected from 1 to 4.

2. The compound of Formula I according to claim 1, wherein R$^1$ is hydrogen.

3. The compound of Formula I according to claim 1, wherein R$^2$ is methyl.

4. The compound of Formula I according to claim 1, wherein X is chloro.

5. The compound of Formula I according to claim 1, wherein n is 1.

6. The compound of Formula I according to claim 1, wherein R$^1$ is hydrogen, R$^2$ is methyl, and X is chloro.

7. The compound of Formula I according to claim 1, wherein the pyridine ring is attached at its 3-position.

8. A compound of claim 6 wherein the pyridine ring is attached at its 3-position.

9. A method for eliciting an anticonvulsant effect in a mammal in need thereof comprising administering to said mammal an effective amount of a compound according to claim 1.

10. A pharmaceutical composition for eliciting an anticonvulsant effect, the composition being in unit dosage form suitable for systemic administration to a mammalian host comprising a pharmaceutical carrier and from about 1 to 500 mg of a compound of claim 1.

* * * * *